(12) United States Patent
Say

(10) Patent No.: US 8,702,932 B2
(45) Date of Patent: Apr. 22, 2014

(54) ELECTROCHEMICAL SENSOR AND METHOD FOR MANUFACTURING

(75) Inventor: James L. Say, Breckenridge, CO (US)

(73) Assignee: Pepex Biomedical, Inc., St. Louis, MO (US)

( * ) Notice: Subject to any disclaimer, the term of this patent is extended or adjusted under 35 U.S.C. 154(b) by 359 days.

(21) Appl. No.: 12/674,858

(22) PCT Filed: Aug. 28, 2008

(86) PCT No.: PCT/US2008/074644
§ 371 (c)(1),
(2), (4) Date: Apr. 18, 2011

(87) PCT Pub. No.: WO2009/032760
PCT Pub. Date: Mar. 12, 2009

(65) Prior Publication Data
US 2011/0189762 A1 Aug. 4, 2011

Related U.S. Application Data

(60) Provisional application No. 60/969,034, filed on Aug. 30, 2007.

(51) Int. Cl.
*G01N 27/30* (2006.01)
*G01N 33/48* (2006.01)

(52) U.S. Cl.
USPC ............. 204/403.1; 204/403.15; 435/287.1; 422/68.1; 422/82.01; 600/345

(58) Field of Classification Search
USPC .............. 204/403.01–403.15, 406, 407; 600/309–365; 435/287.1; 422/68.1, 422/82.01
See application file for complete search history.

(56) References Cited

U.S. PATENT DOCUMENTS 1,454,224 A 5/1923 Schmidt
2,291,720 A 8/1942 Hukle
(Continued)

FOREIGN PATENT DOCUMENTS

DE 101 12 384 A1 9/2002
DE 10 2004 060 742 A1 7/2006
(Continued)

OTHER PUBLICATIONS

European Search Report for 09826755.2 mailed Oct. 5, 2012.
(Continued)

*Primary Examiner* — Jennifer Dieterle
(74) *Attorney, Agent, or Firm* — Merchant & Gould P.C.

(57) ABSTRACT

The present disclosure relates to a sensor including an elongated member including at least a portion that is electrically conductive. The elongated member includes a sensing layer adapted to react with a material desired to be sensed. An insulating layer surrounds the elongated member. The insulating layer defines at least one access opening for allowing the material desired to be sensed to enter an interior region defined between the elongated member and the insulating layer. The insulating layer has an inner transverse cross-sectional profile that is different from an outer transverse cross-sectional profile of the elongated member. The difference in transverse cross-sectional profiles between the elongated member and the insulating layer provides channels at the interior region defined between the insulating layer and the elongated member. The channels extend generally along the length of the elongated member and are sized to allow the material desired to be sensed to move along the length of the sensor.

26 Claims, 9 Drawing Sheets

(56) References Cited

U.S. PATENT DOCUMENTS

| | | |
|---|---|---|
| 3,170,968 A | 2/1965 | Rokunohe et al. |
| 3,766,910 A | 10/1973 | Lake |
| 3,823,035 A | 7/1974 | Sanders |
| 4,008,717 A | 2/1977 | Kowarski |
| 4,073,974 A | 2/1978 | Albarino et al. |
| 4,224,125 A | 9/1980 | Nakamura et al. |
| 4,255,487 A | 3/1981 | Sanders |
| 4,321,057 A | 3/1982 | Buckles |
| 4,399,099 A | 8/1983 | Buckles |
| 4,439,303 A | 3/1984 | Cocchi |
| 4,545,382 A | 10/1985 | Higgins et al. |
| 4,545,835 A | 10/1985 | Gusack et al. |
| 4,552,840 A | 11/1985 | Riffer |
| 4,573,968 A | 3/1986 | Parker |
| 4,640,821 A | 2/1987 | Mody et al. |
| 4,671,288 A | 6/1987 | Gough |
| 4,704,311 A | 11/1987 | Pickering et al. |
| 4,734,184 A | 3/1988 | Burleigh et al. |
| 4,762,603 A | 8/1988 | Morin |
| 4,820,399 A | 4/1989 | Senda et al. |
| 4,824,206 A | 4/1989 | Klainer et al. |
| 4,833,083 A | 5/1989 | Saxena |
| 4,846,548 A | 7/1989 | Klainer |
| 4,880,752 A | 11/1989 | Keck et al. |
| 4,908,115 A | 3/1990 | Morita et al. |
| 4,919,649 A | 4/1990 | Timothy et al. |
| 4,927,516 A | 5/1990 | Yamaguchi et al. |
| 4,945,896 A | 8/1990 | Gade |
| 4,974,929 A | 12/1990 | Curry |
| 4,981,779 A | 1/1991 | Wagner |
| 5,001,054 A | 3/1991 | Wagner |
| 5,002,651 A | 3/1991 | Shaw et al. |
| 5,004,583 A | 4/1991 | Guruswamy et al. |
| RE33,677 E | 8/1991 | Vazirani |
| 5,047,044 A | 9/1991 | Smith et al. |
| 5,112,455 A | 5/1992 | Cozzette et al. |
| 5,131,138 A | 7/1992 | Crouse |
| 5,164,229 A | 11/1992 | Hay et al. |
| 5,165,406 A | 11/1992 | Wong |
| 5,165,407 A | 11/1992 | Wilson et al. |
| 5,171,689 A | 12/1992 | Kawaguri et al. |
| 5,186,808 A | 2/1993 | Yamaguchi et al. |
| 5,205,920 A | 4/1993 | Oyama et al. |
| 5,217,533 A | 6/1993 | Hay et al. |
| 5,220,920 A | 6/1993 | Gharib |
| 5,243,982 A | 9/1993 | Möstl et al. |
| 5,244,636 A | 9/1993 | Walt et al. |
| 5,250,264 A | 10/1993 | Walt et al. |
| 5,262,035 A | 11/1993 | Gregg et al. |
| 5,264,092 A | 11/1993 | Skotheim et al. |
| 5,264,103 A | 11/1993 | Yoshioka et al. |
| 5,264,104 A | 11/1993 | Gregg et al. |
| 5,264,105 A | 11/1993 | Gregg et al. |
| 5,269,891 A | 12/1993 | Colin |
| 5,271,815 A | 12/1993 | Wong |
| 5,271,820 A | 12/1993 | Kinlen et al. |
| 5,277,872 A | 1/1994 | Bankert et al. |
| 5,298,144 A | 3/1994 | Spokane |
| 5,298,741 A | 3/1994 | Walt et al. |
| 5,320,725 A * | 6/1994 | Gregg et al. ............... 205/777.5 |
| 5,320,814 A | 6/1994 | Walt et al. |
| 5,330,634 A | 7/1994 | Wong et al. |
| 5,356,786 A | 10/1994 | Heller et al. |
| 5,366,527 A | 11/1994 | Amos et al. |
| 5,372,133 A | 12/1994 | Hogen Esch |
| D354,347 S | 1/1995 | Knute et al. |
| D354,559 S | 1/1995 | Knute et al. |
| 5,384,028 A | 1/1995 | Ito |
| 5,395,504 A | 3/1995 | Saurer et al. |
| 5,422,246 A | 6/1995 | Koopal et al. |
| 5,431,174 A | 7/1995 | Knute |
| 5,437,973 A | 8/1995 | Vadgama et al. |
| 5,503,728 A | 4/1996 | Kaneko et al. |
| 5,505,828 A | 4/1996 | Wong et al. |
| 5,512,159 A | 4/1996 | Yoshioka et al. |
| 5,515,848 A | 5/1996 | Corbett et al. |
| 5,543,012 A | 8/1996 | Watson et al. |
| 5,575,403 A | 11/1996 | Charlton et al. |
| 5,593,852 A | 1/1997 | Heller et al. |
| 5,605,152 A | 2/1997 | Slate et al. |
| 5,609,749 A | 3/1997 | Yamauchi et al. |
| 5,645,710 A | 7/1997 | Shieh |
| 5,656,241 A | 8/1997 | Seifert et al. |
| 5,720,924 A | 2/1998 | Eikmeier et al. |
| 5,777,060 A | 7/1998 | Van Antwerp |
| 5,810,199 A | 9/1998 | Charlton et al. |
| 5,814,601 A | 9/1998 | Winslow et al. |
| 5,849,415 A | 12/1998 | Shalaby et al. |
| 5,863,800 A | 1/1999 | Eikmeier et al. |
| 5,900,215 A | 5/1999 | Seifert et al. |
| 5,951,764 A | 9/1999 | Hay et al. |
| 5,971,941 A | 10/1999 | Simons et al. |
| 5,972,199 A | 10/1999 | Heller et al. |
| 5,982,959 A | 11/1999 | Hopenfeld |
| 5,997,501 A | 12/1999 | Gross et al. |
| 6,036,924 A | 3/2000 | Simons et al. |
| 6,044,665 A | 4/2000 | Lysson et al. |
| 6,048,352 A | 4/2000 | Douglas et al. |
| D424,696 S | 5/2000 | Ray et al. |
| D426,638 S | 6/2000 | Ray et al. |
| 6,071,294 A | 6/2000 | Simons et al. |
| 6,071,391 A | 6/2000 | Gotoh et al. |
| 6,083,710 A | 7/2000 | Heller et al. |
| 6,099,484 A | 8/2000 | Douglas et al. |
| 6,103,033 A | 8/2000 | Say et al. |
| 6,103,199 A | 8/2000 | Bjornson et al. |
| 6,104,940 A | 8/2000 | Watanabe et al. |
| 6,107,083 A | 8/2000 | Collins et al. |
| 6,120,676 A | 9/2000 | Heller et al. |
| 6,143,164 A | 11/2000 | Heller et al. |
| 6,241,863 B1 | 6/2001 | Montbouquette |
| 6,299,757 B1 | 10/2001 | Feldman et al. |
| 6,329,161 B1 | 12/2001 | Heller et al. |
| 6,338,790 B1 | 1/2002 | Feldman et al. |
| 6,349,229 B1 | 2/2002 | Watanabe et al. |
| 6,379,317 B1 | 4/2002 | Kintzig et al. |
| 6,461,496 B1 | 10/2002 | Feldman et al. |
| 6,464,849 B1 | 10/2002 | Say et al. |
| 6,503,381 B1 | 1/2003 | Gotoh et al. |
| 6,560,471 B1 | 5/2003 | Heller et al. |
| 6,561,989 B2 | 5/2003 | Whitson |
| 6,576,101 B1 | 6/2003 | Heller et al. |
| 6,591,125 B1 | 7/2003 | Buse et al. |
| 6,592,745 B1 | 7/2003 | Feldman et al. |
| 6,607,658 B1 | 8/2003 | Heller et al. |
| 6,610,978 B2 | 8/2003 | Yin et al. |
| 6,616,819 B1 | 9/2003 | Liamos et al. |
| 6,618,934 B1 | 9/2003 | Feldman et al. |
| 6,620,112 B2 | 9/2003 | Klitmose |
| 6,676,816 B2 | 1/2004 | Mao et al. |
| 6,706,159 B2 | 3/2004 | Moerman et al. |
| 6,707,554 B1 | 3/2004 | Miltner et al. |
| 6,740,214 B1 | 5/2004 | Dobson et al. |
| 6,749,740 B2 | 6/2004 | Liamos et al. |
| 6,783,502 B2 | 8/2004 | Orloff et al. |
| 6,840,912 B2 | 1/2005 | Kloepfer et al. |
| 6,881,551 B2 | 4/2005 | Heller et al. |
| 6,893,545 B2 | 5/2005 | Gotoh et al. |
| 6,965,791 B1 * | 11/2005 | Hitchcock et al. ............ 600/345 |
| 7,008,799 B1 | 3/2006 | Zimmer et al. |
| 7,058,437 B2 | 6/2006 | Buse et al. |
| 7,211,437 B2 | 5/2007 | Schabbach et al. |
| 7,264,139 B2 | 9/2007 | Brickwood et al. |
| 7,282,705 B2 | 10/2007 | Brennen |
| 7,299,081 B2 | 11/2007 | Mace et al. |
| 7,322,942 B2 | 1/2008 | Roe |
| 7,335,294 B2 | 2/2008 | Heller et al. |
| 7,344,499 B1 | 3/2008 | Prausnitz et al. |
| 7,378,007 B2 | 5/2008 | Moerman et al. |
| 7,396,334 B2 | 7/2008 | Kuhr et al. |
| 7,585,278 B2 | 9/2009 | Aceti et al. |
| 7,723,099 B2 | 5/2010 | Miller et al. |
| 7,740,581 B2 | 6/2010 | Buse et al. |
| 7,828,749 B2 | 11/2010 | Douglas et al. |

(56) References Cited

U.S. PATENT DOCUMENTS

| | | | |
|---|---|---|---|
| 7,829,023 | B2 | 11/2010 | Burke et al. |
| 7,860,544 | B2 | 12/2010 | Say et al. |
| 2002/0040208 | A1 | 4/2002 | Flaherty et al. |
| 2002/0098124 | A1 | 7/2002 | Bentsen et al. |
| 2003/0211619 | A1 | 11/2003 | Olson et al. |
| 2004/0087033 | A1 | 5/2004 | Schembri |
| 2004/0102717 | A1 | 5/2004 | Qi |
| 2004/0236251 | A1 | 11/2004 | Roe et al. |
| 2005/0023137 | A1* | 2/2005 | Bhullar et al. ............ 204/403.1 |
| 2005/0067737 | A1 | 3/2005 | Rappin et al. |
| 2005/0089944 | A1 | 4/2005 | Shieh et al. |
| 2005/0196747 | A1 | 9/2005 | Stiene |
| 2005/0197548 | A1 | 9/2005 | Dietiker |
| 2005/0238537 | A1 | 10/2005 | Say et al. |
| 2006/0241517 | A1 | 10/2006 | Fowler et al. |
| 2007/0027385 | A1 | 2/2007 | Brister et al. |
| 2007/0123803 | A1 | 5/2007 | Fujiwara et al. |
| 2007/0149897 | A1 | 6/2007 | Ghesquiere et al. |
| 2007/0199818 | A1* | 8/2007 | Petyt et al. ............ 204/403.01 |
| 2007/0218281 | A1 | 9/2007 | Demir et al. |
| 2008/0017645 | A1 | 1/2008 | Garagiola |
| 2008/0097546 | A1 | 4/2008 | Powers et al. |
| 2008/0167578 | A1 | 7/2008 | Bryer et al. |
| 2009/0021901 | A1 | 1/2009 | Stothers |
| 2009/0032760 | A1 | 2/2009 | Muscatell |
| 2009/0069654 | A1 | 3/2009 | Yasuzawa et al. |
| 2009/0178923 | A1* | 7/2009 | Marquant et al. ........ 204/403.01 |
| 2009/0257917 | A1 | 10/2009 | Nakamura et al. |
| 2010/0018869 | A1 | 1/2010 | Feldman et al. |
| 2010/0018871 | A1 | 1/2010 | Feldman et al. |
| 2010/0051479 | A1 | 3/2010 | Heller et al. |
| 2010/0059372 | A1 | 3/2010 | Heller et al. |
| 2010/0059373 | A1 | 3/2010 | Heller et al. |
| 2010/0072063 | A1 | 3/2010 | Heller et al. |
| 2010/0072064 | A1 | 3/2010 | Heller et al. |
| 2010/0326842 | A1 | 12/2010 | Mazza et al. |
| 2011/0028815 | A1 | 2/2011 | Simpson et al. |
| 2011/0086373 | A1 | 4/2011 | Wallace-Davis et al. |
| 2011/0203941 | A1* | 8/2011 | Say ............................ 205/775 |
| 2011/0265944 | A1 | 11/2011 | Say |
| 2011/0266149 | A1 | 11/2011 | Say |
| 2011/0270061 | A1 | 11/2011 | Say |
| 2012/0291254 | A1 | 11/2012 | Say |

FOREIGN PATENT DOCUMENTS

| | | |
|---|---|---|
| EP | 0 256 415 A2 | 2/1988 |
| EP | 0 327 658 A1 | 8/1989 |
| EP | 0 409 033 A2 | 1/1991 |
| EP | 0 420 296 A1 | 4/1991 |
| EP | 0 592 805 A2 | 4/1994 |
| EP | 0 710 835 A2 | 5/1996 |
| EP | 0 792 620 A2 | 9/1997 |
| EP | 0 965 031 A1 | 12/1999 |
| EP | 0 965 301 A1 | 12/1999 |
| EP | 1 462 775 B1 | 12/2007 |
| JP | 64-3552 | 1/1989 |
| JP | 1-153952 | 6/1989 |
| JP | 1-263537 | 10/1989 |
| JP | 4-279854 | 10/1992 |
| JP | 6-174946 | 6/1994 |
| JP | 8-107890 | 4/1996 |
| JP | 2007-202632 | 8/2007 |
| WO | WO 89/07139 | 8/1989 |
| WO | WO 91/15993 | 10/1991 |
| WO | WO 94/10553 | 5/1994 |
| WO | WO 96/06947 | 3/1996 |
| WO | WO 96/22730 | 8/1996 |
| WO | WO 96/39616 | 12/1996 |
| WO | WO 97/15827 | 5/1997 |
| WO | WO 00/35340 | 6/2000 |
| WO | WO 2005/051183 A1 | 6/2005 |
| WO | WO 2007/091633 A1 | 8/2007 |
| WO | WO 2008/017645 * | 2/2008 |
| WO | WO 2008/017645 A1 | 2/2008 |
| WO | WO 2009/032760 A2 | 3/2009 |
| WO | WO 2009/051901 | 4/2009 |
| WO | WO 2010/056869 A2 | 5/2010 |
| WO | WO 2010/056876 A2 | 5/2010 |
| WO | WO 2010/056878 A2 | 5/2010 |

OTHER PUBLICATIONS

International Search Report and Written Opinion for PCT/US2008/074649 mailed Apr. 20, 2009.

International Search Report and Written Opinion for PCT/US2008/074644 mailed May 14, 2009.

International Search Report and Written Opinion for PCT/US2009/064216 mailed May 3, 2010.

International Search Report and Written Opinion for PCT/US2009/064225 mailed May 4, 2010.

International Search Report and Written Opinion for PCT/US2009/064228 mailed Jul. 1, 2010.

Gough et al., "Short-term In Vivo operation of a glucose sensor," *A.S.A.I.O. Transactions* (1986) 32 (1): 148-150. XP000009622.

Jaraba et al., "NADH amperometric sensor based on poly(3-methylthiophene)-coated cylindrical carbon fiber microelectrodes: application to the enzymatic determination of L-lactate," *Electrochimica Acta.* (1998) 43 (23): 3555-3565.

Netchiporouk et al., "Properties of carbon fibre microelectrodes as a basis for enzyme biosensors," *Analytica Chimica Acta* (1995) 303: 275-283.

Sakslund et al, "Analysis of the factors determining the sensitivity of a miniaturized glucose biosensor made by codeposition of palladium and glucose oxidase onto an 8 µm carbon filter," *Journal of Electroanalytical Chemistry* (1996) 402: 149-160.

Sakslund et al., "Development and evaluation of glucose microsensors based on electrochemical codeposition of ruthenium and glucose oxidase onto carbon fiber microelectrodes," *Journal of Electroanalytical Chemistry* (1995) 397: 149-155.

* cited by examiner

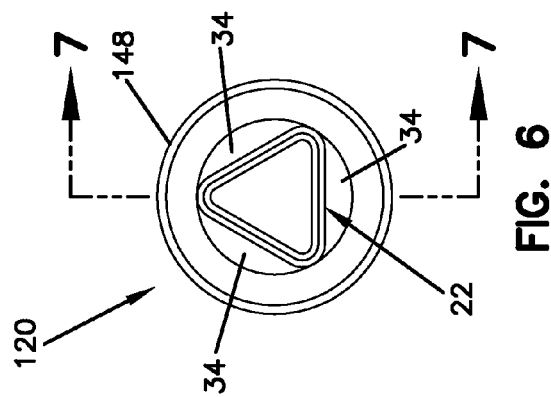
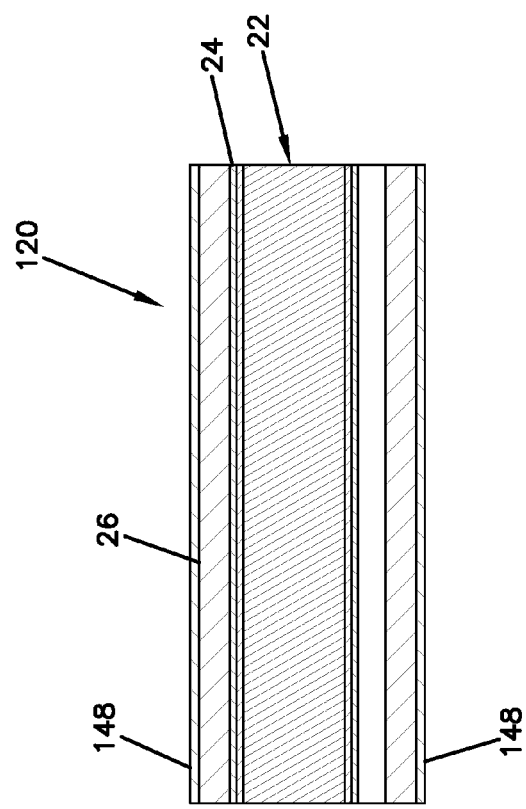
FIG. 6
FIG. 7

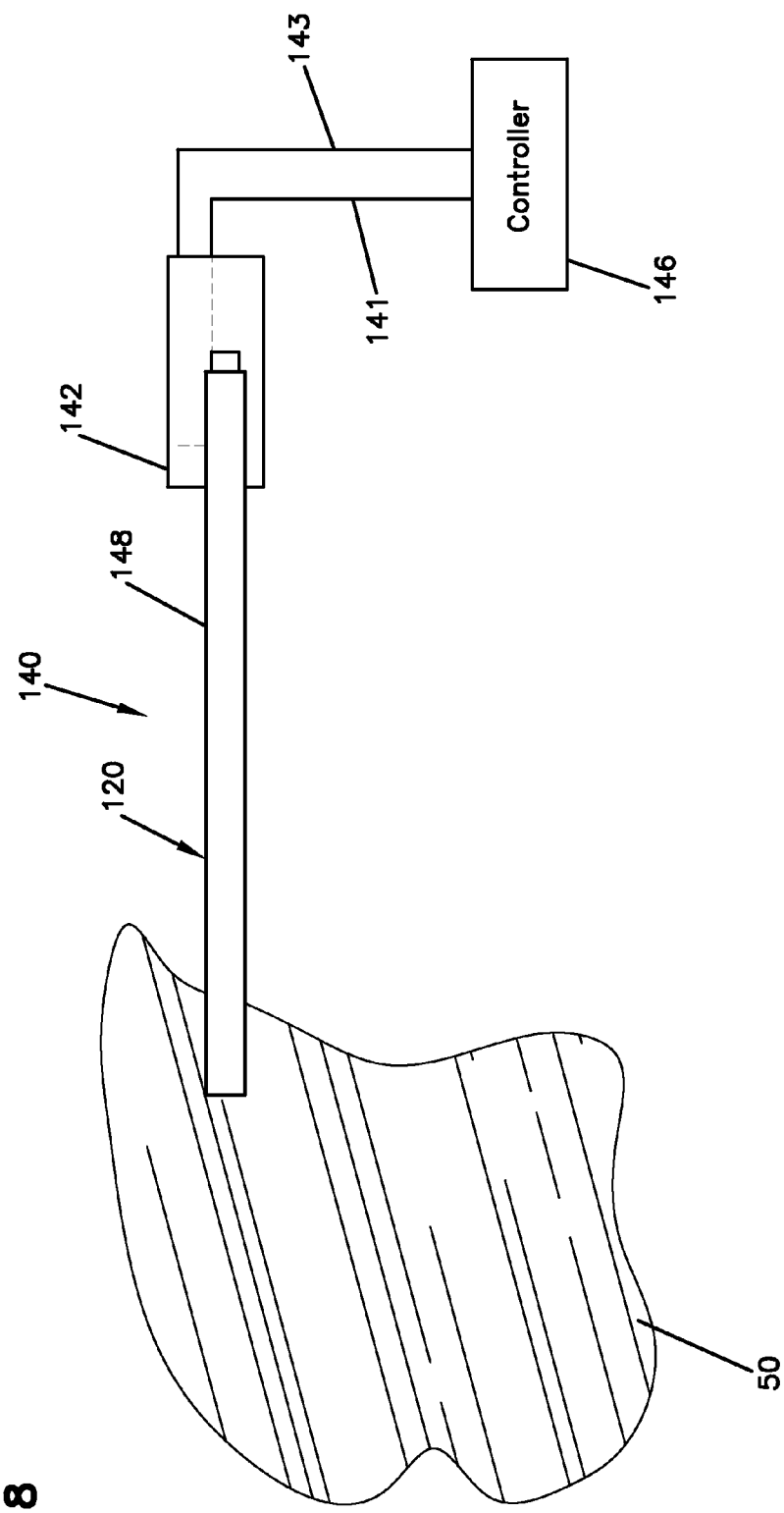

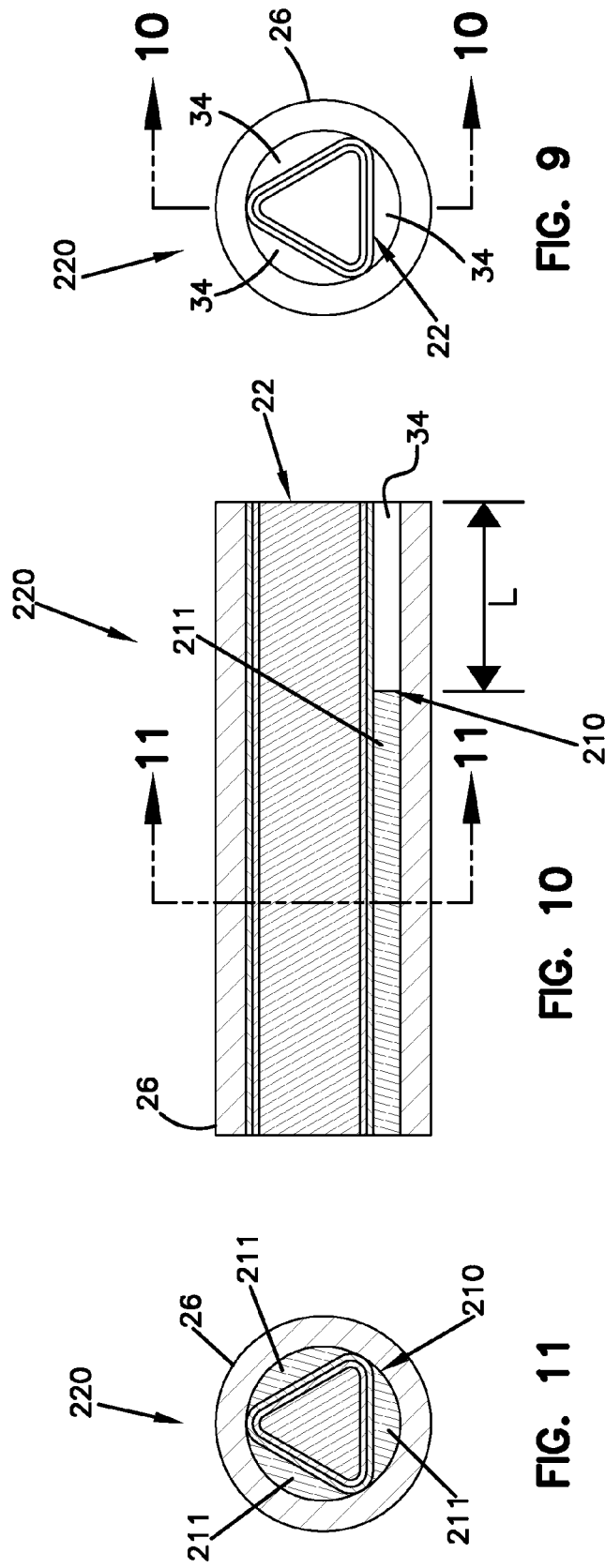

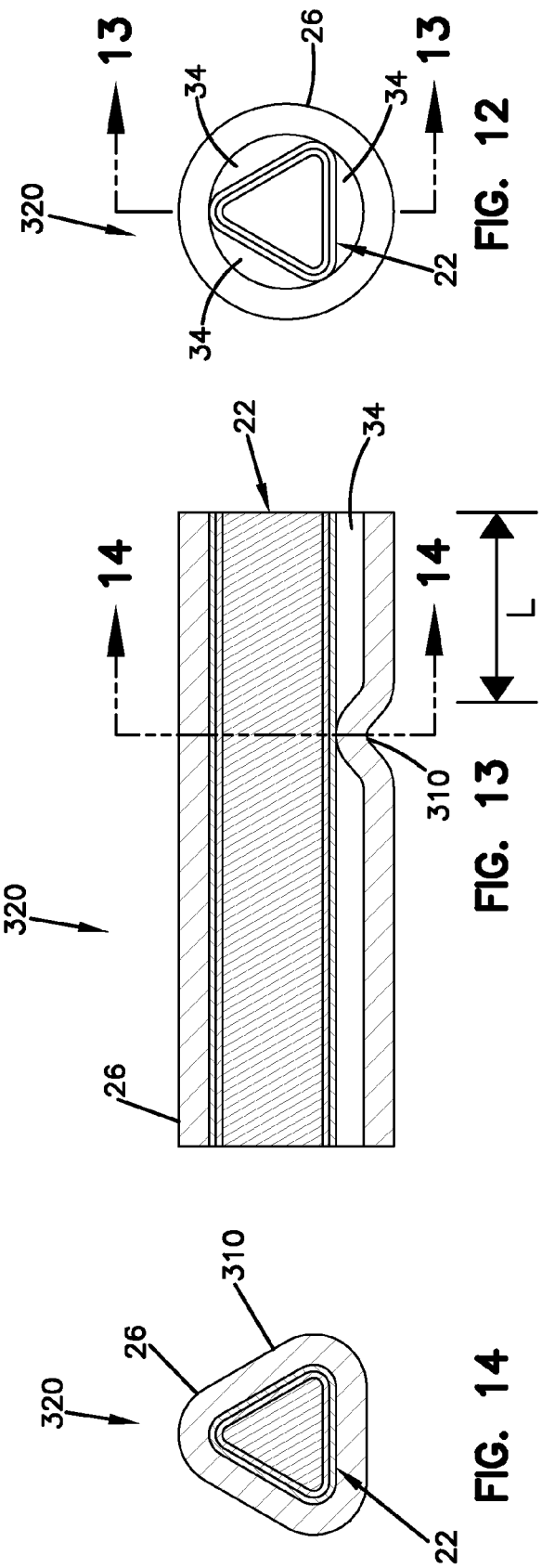

ELECTROCHEMICAL SENSOR AND METHOD FOR MANUFACTURING

This application is a National Stage Application of PCT/US2008/074644, filed Aug. 28, 2008 which claims the benefit of U.S. Provisional patent application Ser. No. 60/969,034, filed Aug. 30, 2007. To the extent appropriate, a claim of priority is made to each of the above disclosed applications.

TECHNICAL FIELD

The present disclosure relates to sensors for measuring bioanalytes and to methods for making such sensors.

BACKGROUND

Electrochemical bio-sensors have been developed for detecting analyte concentrations in a given fluid sample. For example, U.S. Pat. Nos. 5,264,105; 5,356,786; 5,262,035; 5,320,725; and 6,464,849, which are hereby incorporated by reference in their entireties, disclose wired enzyme sensors for detecting analytes such as lactate or glucose. Technology adapted for enhancing sensor miniaturization and durability is desirable.

SUMMARY

One aspect of the present disclosure relates to an electrochemical sensor including a sensing layer provided on an at least partially conductive fiber having a non-circular transverse cross-sectional profile.

Another aspect of the present disclosure relates to a sensor including an elongated member including at least a portion that is electrically conductive. The elongated member including a sensing layer adapted to react with a material desired to be sensed. An insulating layer surrounds the elongated member. The insulating layer defines at least one access opening for allowing the material desired to be sensed to enter an interior region defined between the elongated member and the insulating layer. The insulating layer has an inner transverse cross-sectional profile that is different from an outer transverse cross-sectional profile of the elongated member. The difference in transverse cross-sectional profiles between the elongated member and the insulating layer provides channels at the interior region defined between the insulating layer and the elongated member. The channels extend generally along the length of the elongated member and are sized to allow the material desired to be sensed to move along the length of the sensor.

A variety of additional inventive aspects will be set forth in the description that follows. The inventive aspects can relate to individual features and to combinations of features. It is to be understood that both the foregoing general description and the following detailed description are exemplary and explanatory only and are not restrictive of the broad inventive concepts upon which the embodiments disclosed herein are based.

BRIEF DESCRIPTION OF THE DRAWINGS

FIG. 6 is an end view showing the sensing tip of a second sensor having features that are examples of inventive aspects in accordance with the principles of the present disclosure;

FIG. 7 is a cross-sectional view taken along section line 7-7 of FIG. 6;

FIG. 8 is a schematic view of a sensor system incorporating the sensor of FIG. 6;

FIG. 9 is an end view showing the sensing tip of a third sensor having features that are examples of inventive aspects in accordance with the principles of the present disclosure;

FIG. 10 is a cross-sectional view taken along section-line 10-10 of FIG. 9;

FIG. 11 is a cross-sectional view taken along section line 11-11 of FIG. 10;

FIG. 12 is an end view showing the sensing tip of a fourth sensor having features that are examples of inventive aspects in accordance with the principles of the present disclosure;

FIG. 13 is a cross-sectional view taken along section-line 13-13 of FIG. 12;

FIG. 14 is a cross-sectional view taken along section line 14-14 of FIG. 13;

DETAILED DESCRIPTION

Figure 1:
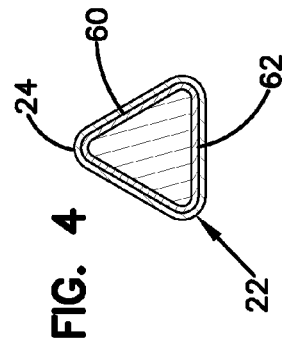
FIG. 1 is a perspective view showing a sensing tip of a first sensor having features that are examples of inventive aspects in accordance with the principles of the present disclosure.

Reference will now be made in detail to exemplary aspects of the present disclosure which are illustrated in the accompanying drawings. Wherever possible, the same reference numbers will be used throughout the drawings to refer to the same or like parts.

The following definitions are provided for terms used herein:

A "working electrode" is an electrode at which the analyte (or a second compound whose level depends on the level of the analyte) is electrooxidized or electroreduced with or without the agency of an electron transfer agent.

A "reference electrode" is an electrode used in measuring the potential of the working electrode. The reference electrode should have a generally constant electrochemical potential as long as no current flows through it. As used herein, the term "reference electrode" includes pseudo-reference electrodes. In the context of the disclosure, the term "reference electrode" can include reference electrodes which also function as counter electrodes (i.e., a counter/reference electrode).

A "counter electrode" refers to an electrode paired with a working electrode to form an electrochemical cell. In use, electrical current passes through the working and counter electrodes. The electrical current passing through the counter electrode is equal in magnitude and opposite in sign to the current passing through the working electrode. In the context of the disclosure, the term "counter electrode" can include counter electrodes which also function as reference electrodes (i.e., a counter/reference electrode).

A "counter/reference electrode" is an electrode that functions as both a counter electrode and a reference electrode.

An "electrochemical sensing system" is a system configured to detect the presence and/or measure the level of an analyte in a sample via electrochemical oxidation and reduction reactions on the sensor. These reactions are transduced to an electrical signal that can be correlated to an amount, concentration, or level of an analyte in the sample. Further details about electrochemical sensing systems, working electrodes, counter electrodes and reference electrodes can be found at U.S. Pat. No. 6,560,471, that is hereby incorporated by reference in its entirety.

"Electrolysis" is the electrooxidation or electroreduction of a compound either directly at an electrode or via one or more electron transfer agents.

An "electron transfer agent" is a compound that carries electrons between the analyte and the working electrode, either directly, or in cooperation with other electron transfer agents. One example of an electron transfer agent is a redox mediator.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both. In some embodiments, the sensing layer has a generally dry or non-hydrated state prior to use. In such embodiments, the sensing layer can be hydrated during use by water within the fluid sample being tested.

FIGS. 1-4 illustrate a sensor 20 having features that are examples of inventive aspects in accordance with the principles of the present disclosure. The sensor 20 includes an elongated member 22 having at least a portion that is electrically conductive and that functions as a working electrode. The elongated member 22 can include a sensing layer 24 that covers or is positioned adjacent to the working electrode. An insulating layer 26 surrounds the elongated member 22. The sensor 20 includes a sensing tip 28 at which the insulating layer 26 does not cover/enclose the elongated member 22 (e.g., the tip of the elongated member 22 is exposed). This open tip configuration provides an access opening 30 at the sensing tip 28 for allowing the material desired to be sensed to enter an interior region 32 of the sensor 20. The interior region 32 is defined between the elongated member 22 and the insulating layer 26. The sensor 20 also includes a base end 29 positioned opposite from the sensing tip 28.

Figure 2:
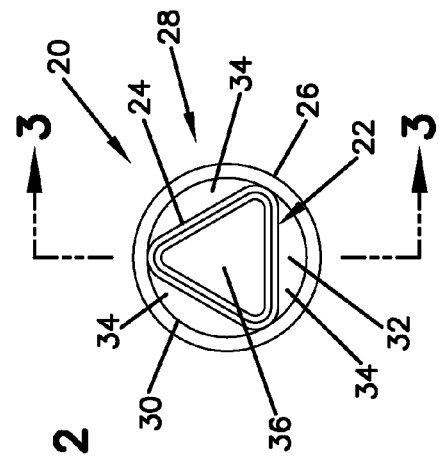
FIG. 2 is an end view showing the sensing tip of the sensor of FIG. 1.
Figure 4:
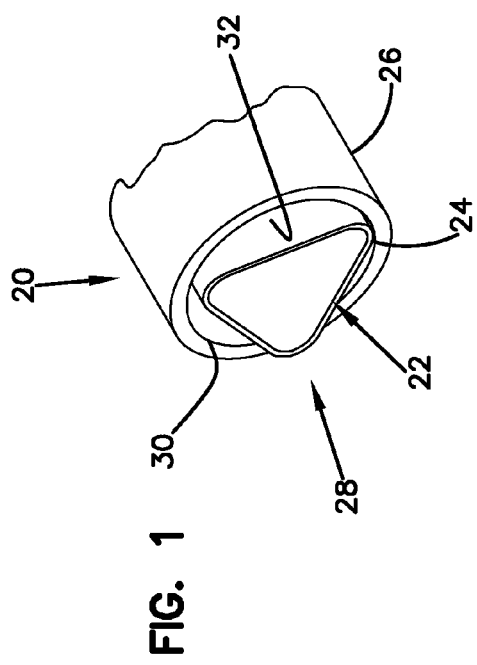
FIG. 4 is a transverse cross-sectional view of a fiber used within the sensor of FIG. 1, the fiber is shown covered with a layer of sensing chemistry.
Figure 3:
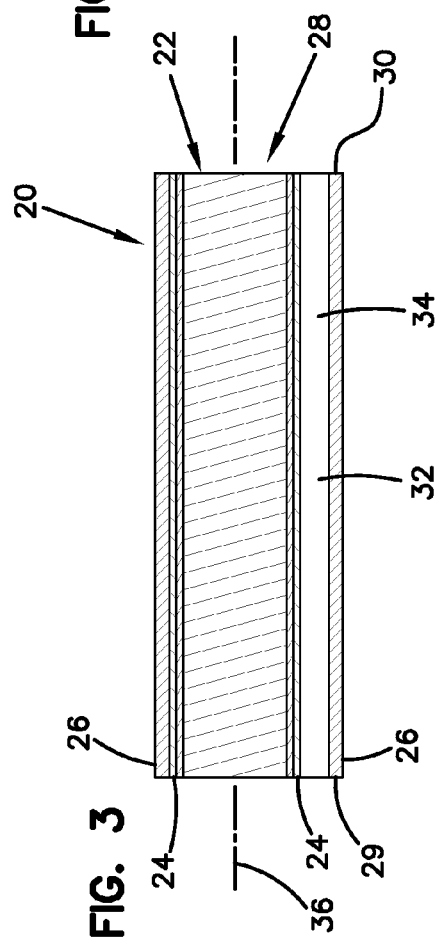
FIG. 3 is a cross-sectional view taken along section-line 3-3 of FIG. 2.

Referring to FIG. 2, the insulating layer 26 has an inner transverse cross-sectional profile that is different from an outer transverse cross-sectional profile of the elongated member 22. For example, in the embodiment of FIGS. 1-4, the inner transverse cross-sectional profile of the insulating layer 26 is generally circular, while the outer transverse cross-sectional profile of the elongated member 22 is generally triangular. The difference in transverse cross-sectional profiles between the elongated member 22 and the insulating layer 26 provides channels 34 at the interior region 32 defined between the insulating layer 26 and the elongated member 22. The channels 34 extend generally along the length (i.e., generally along a central longitudinal axis 36 of the sensor 20) of the elongated member 22 and are sized to allow the material desired to be sensed to move through the interior region 32 along the length of the sensor 20. In other embodiments, the shapes could be reversed such that the cross-sectional profile of the insulating layer is generally triangular and the cross-sectional profile of the elongated member is generally circular. In other embodiments, other cross-sectional profile shapes (e.g., other multi-sided shapes such as squares, rectangles, pentagons, octagons, etc.) could be used.

Figure 5:
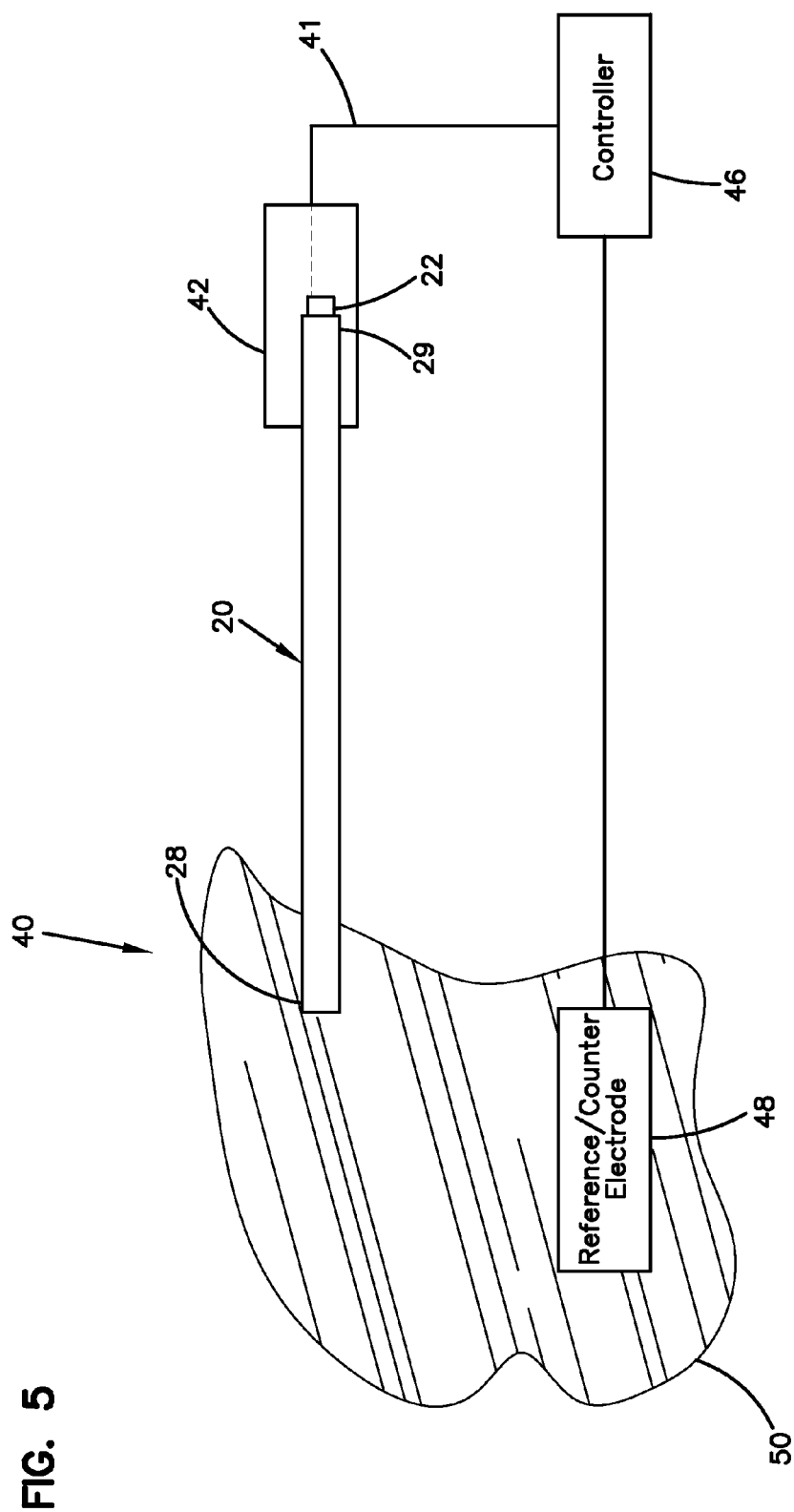
FIG. 5 is a schematic view of a sensor system incorporating the sensor of FIG. 1.

FIG. 5 illustrates an electrochemical sensing system 40 that incorporates the sensor 20 of FIGS. 1-4. The working electrode of the elongated member 22 is electrically connected to a wire 41 by a connector or hub 42 positioned at the base end 29 of the sensor 20. The wire 41 electrically connects the working electrode of the elongated member 22 to a controller 46. The controller 46 can be any type of controller such as a micro-controller, a mechanical controller, a software driven controller, a hardware driven controller, a firmware driven controller, etc. The controller can include a microprocessor that interfaces with memory. The controller 46 is also electrically connected to a counter electrode 48. In one embodiment, the counter electrode is only a counter electrode. In other embodiments, the counter electrode 48 can function as a counter/reference electrode and can include a layer of silver silver-chloride.

In use of the sensing system 40, the sensing tip 28 of the sensor 20 is immersed within a test volume 50 of a liquid sample (e.g., a blood sample) containing an analyte desired to be sensed. The sample may be an ex vivo or in vivo sample. The test volume 50 is the volume from which the analyte desired to be sensed can diffuse into the sensor 20 during the sensing period. With the sensor 20 so positioned, the liquid sample enters the channels 34 through the sensing tip 28 and can move along the lengths of the channels 34 (e.g., by capillary action) in a direction from the sensing tip 28 toward the base end 29. Water within the test volume 50 can diffuse into the sensing layer 24 such that the sensing layer 24 is hydrated. The analyte within the test volume 50 also diffuses into the sensing layer 24. A voltage potential is then applied between the counter electrode 48 and the working electrode. When the potential is applied, an electrical current will flow through the test volume 50 between the counter electrode 48 and the working electrode. The current is a result of the oxidation or reduction of the analyte in the test volume 50. This electrochemical reaction occurs via the electron transfer agent in the sensing layer 24 and the optional electron transfer catalyst/enzyme in the sensing layer 24. By measuring the current flow generated at a given potential, the concentration of a given analyte in the test sample can be determined. Those skilled in the art will recognize that current measurements can be obtained by a variety of techniques including, among other things, coulometric, potentiometric, amperometric, voltammetric, and other electrochemical techniques.

When the voltage potential is applied between the working and counter electrodes, the analyte within the interior region 32 reacts with the sensing layer 24 and is consumed. Thereafter, additional analyte from the test volume 50 diffuses into the interior region 32 through the open sensing tip 28. As the analyte enters the interior region 32, the analyte reacts with the portion of the sensing layer 24 located closest to the sensing tip 28 and is consumed before the analyte can migrate further into the sensor along the channels 34. In this way, the open tip configuration of the insulating layer 26 extends sensor life by limiting the amount of the sensor layer 24 that is exposed to the analyte at a given moment in time. Over time, the portion of the sensing layer 24 that is closest to the sensing tip 28 is depleted. When this occurs, the analyte is able to move further along the channels 32 (i.e., deeper into the sensor) to reach an active portion of the sensor layer 24. This process continues until the analyte depletes the sensing layer 24 along the entire lengths of the channels 34 and the life of the sensor ends. In this progression, the portion of the sensing layer 24 located at the deepest portion of the sensor (i.e., the interior region 32 closest to the base end 29) is the last portion of the sensing layer 24 to be depleted.

To oxidize or reduce the analyte, a potential (versus a reference potential) is applied across the working and counter electrodes. The minimum magnitude of the applied potential is often dependent on the particular electron transfer agent, analyte (if the analyte is directly oxidized or reduced at the electrode), or second compound (if a second compound, such as oxygen or hydrogen peroxide, whose level is dependent on the analyte level, is directly oxidized or reduced at the electrode). The applied potential usually equals or is more oxidizing or reducing, depending on the desired electrochemical reaction, than the redox potential of the electron transfer agent, analyte, or second compound, whichever is directly oxidized or reduced at the electrode. The potential at the working electrode is typically large enough to drive the electrochemical reaction to or near completion. When a potential is applied between the working electrode and the counter electrode, an electrical current will flow. The current is a result of the reduction or oxidation of the analyte or a second compound whose level is affected by the analyte. In one embodiment, the electrochemical reaction occurs via an electron transfer agent and the optional catalyst.

In certain embodiments, the elongated member 22 of the sensor 20 can include an electrically conductive wire or fiber. For example, the elongated member 22 can include a metal wire or a glassy carbon fiber. In a preferred embodiment shown at FIG. 4, the elongated member 22 has a composite structure and includes a fiber having a dielectric core 60 surrounded by a conductive layer 62 which forms the working electrode of the sensor 20. A preferred composite fiber is sold under the name Resistat® by Shakespeare Conductive Fibers LLC. This composite fiber includes a composite nylon monofilament conductive thread material made conductive by the suffusion of about a 1 micron layer of carbonized nylon isomer onto a dielectric nylon core material. The Resistat® material is comprised of isomers of nylon to create the basic 2 layer composite thread. However, many other polymers are available for the construction such as: polyethylene terephthalate, nylon 6, nylon 6,6, cellulose, polypropylene cellulose acetate, polyacrylonitrile and copolymers of polyacrylonitrile for a first component and polymers such as of polyethylene terephthalate, nylon 6, nylon 6,6, cellulose, polypropylene cellulose acetate, polyacrylonitrile and copolymers of polyacrylonitrile as constituents of a second component. Inherently conductive polymers (ICP) such as doped polyanaline or polypyrolle can be incorporated into the conductive layer along with the carbon to complete the formulation. In certain embodiments, the ICP can be used as the electrode surface alone or in conjunction with carbon. The Resistat® fiber product is currently sold with a circular transverse cross-sectional profile. By post forming or extruding the Resistat® fiber, other transverse cross-sectional profiles (e.g., generally triangular) can be provided. The Resistat® fiber is availability in diameters of 0.0025 to 0.016 inches, which as suitable for sensors in accordance with the principles of the present disclosure. Example patents disclosing composite fibers suitable for use in practicing sensors in accordance with the principles of the present disclosure include U.S. Pat. Nos. 3,823,035; 4,255,487; 4,545,835 and 4,704,311, which are hereby incorporated by reference.

The sensing layer 24 preferably includes a sensing chemistry such as a redox compound or mediator. The term redox compound is used herein to mean a compound that can be oxidized or reduced. Exemplary redox compounds include transition metal complexes with organic ligands. Preferred redox compounds/mediators are osmium transition metal complexes with one or more ligands having a nitrogen containing heterocycle such as 2,2'-bipyridine. The sensing material can also include a redox enzyme. A redox enzyme is an enzyme that catalyzes an oxidation or reduction of an analyte. For example, a glucose oxidase or glucose dehydrogenase can be used when the analyte is glucose. Also, a lactate oxidase or lactate dehydrogenase fills this role when the analyte is lactate. In systems such as the one being described, these enzymes catalyze the electrolysis of an analyte by transferring electrons between the analyte and the electrode via the redox compound. Further information regarding sensing chemistry can be found at U.S. Pat. Nos. 5,264,105; 5,356,786; 5,262,035; and 5,320,725, which were previously incorporated by reference in their entireties.

The insulating layer 26 of the sensor 20 preferably serves numerous functions to the sensor 20. For example, the insulating layer 26 preferably electrically insulates the elongated member 22. Additionally, the insulating layer 26 preferably provides mechanical strength for protecting the elongated member 22. Also, as described above, the insulating layer 26 preferably forms a barrier about the elongated member 22 that prevents the uncontrolled transport of a substance desired to be sensed (e.g., an analyte such as glucose or lactate) to the sensing layer 24. In one nonlimiting embodiment, the insulating layer 26 is made of a polymeric material such as polyimide, polyurethane or other materials. In certain embodiments, the insulating layer 26 can have a maximum outer dimension (e.g., an outer diameter) less than 0.02 inches. In other embodiments, the channels 34 defined between the elongated member 22 and the insulating layer 26 can each have a transverse cross-sectional area less than or equal to 26,000 square microns. In other embodiments, the ratio of perimeter arc section (defined by the inner diameter of the insulating layer 26) to chord length (defined by a side of the elongated member 22) is about 1.2:1.

It will be appreciated that the sensor 20 can be used for ex vivo or in vivo applications. In certain embodiments, the sensor 20 can be incorporated into a peripheral catheter to provide on-line monitoring of bioanalytes in the same manner described in U.S. Pat. No. 6,464,849, that was previously incorporated by reference herein.

FIGS. 6 and 7 show a second electro-chemical sensor 120 having features that are examples of inventive aspects in accordance with the principles of the present disclosure. The sensor 120 has the same configuration as the sensor of FIGS. 1-4, except a counter electrode 148 has been provided at the outer surface of the insulating layer 26. It will be appreciated that the counter electrode can only function as a counter electrode, or could also function as a counter/reference electrode. The counter electrode 148 is made of an electrically conductive material coated or otherwise provided about the exterior of the insulation layer 26. In the case where the counter electrode functions as a counter reference electrode, the electrode 148 is formed by depositing silver silver-chloride about the exterior of the insulating layer 26.

FIG. 8 shows an electrical sensing system 140 that incorporates the sensor 120 of FIGS. 6 and 7. The working electrode of the sensor 120 is electrically connected to a wire 141 by a hub 142 positioned at a base end of the sensor 120. The wire 141 electrically connects the working electrode of the sensor 120 to a controller 146. The hub 142 also electrically connects the counter electrode 148 to a wire 143 that electrically connects the counter electrode 148 to the controller 146. As shown at FIG. 8, the open sensing tip of the sensor 120 is shown within a test sample 50.

FIGS. 9-11 show a third electro-chemical sensor 220 having features that are examples of inventive aspects in accordance with the principles of the present disclosure. The sensor 220 has the same construction as the sensor 20 of FIGS. 1-4, except a stop arrangement 210 has been provided within the interior region 32 to limit the distance the sample fluid can move along the length of the sensor 220. The stop arrangement 210 includes blocking portions 211 that fill the channels 34 at a desired location so that sample fluid flow is prevented from moving past the stop arrangement 210. As shown in FIG. 10, the stop arrangement 210 prevents the test fluid from flowing within the channels 34 for a distance greater than a length L. In one embodiment, the blocking elements 211 are made of a material such as polytetrafluoroethylene that allows air to pass through the stop arrangement but does not allow fluid to pass through the stop arrangement.

FIGS. 12-14 show a fourth sensor 320 having features that are examples of inventive aspects in accordance with the principles of the present disclosure. The sensor 320 has the same construction as the sensor 20 of FIGS. 1-4, except a crimp 310 has been provided around the exterior of the sensor 320 to limit the length L that a fluid desired to be tested can flow into the sensor 320. The crimp 310 causes the insulating layer 26 to be compressed against the elongated member 22 thereby closing the channels 34 at the crimp location 310. Air holes can be formed through the insulating layer 26 adjacent the crimp location 310 to allow air to exit the channels 34 when the channels 34 are being filled with test fluid. It will be appreciated that the holes are preferably small enough to prevent the passage of the sample fluid therethrough.

Figure 15:
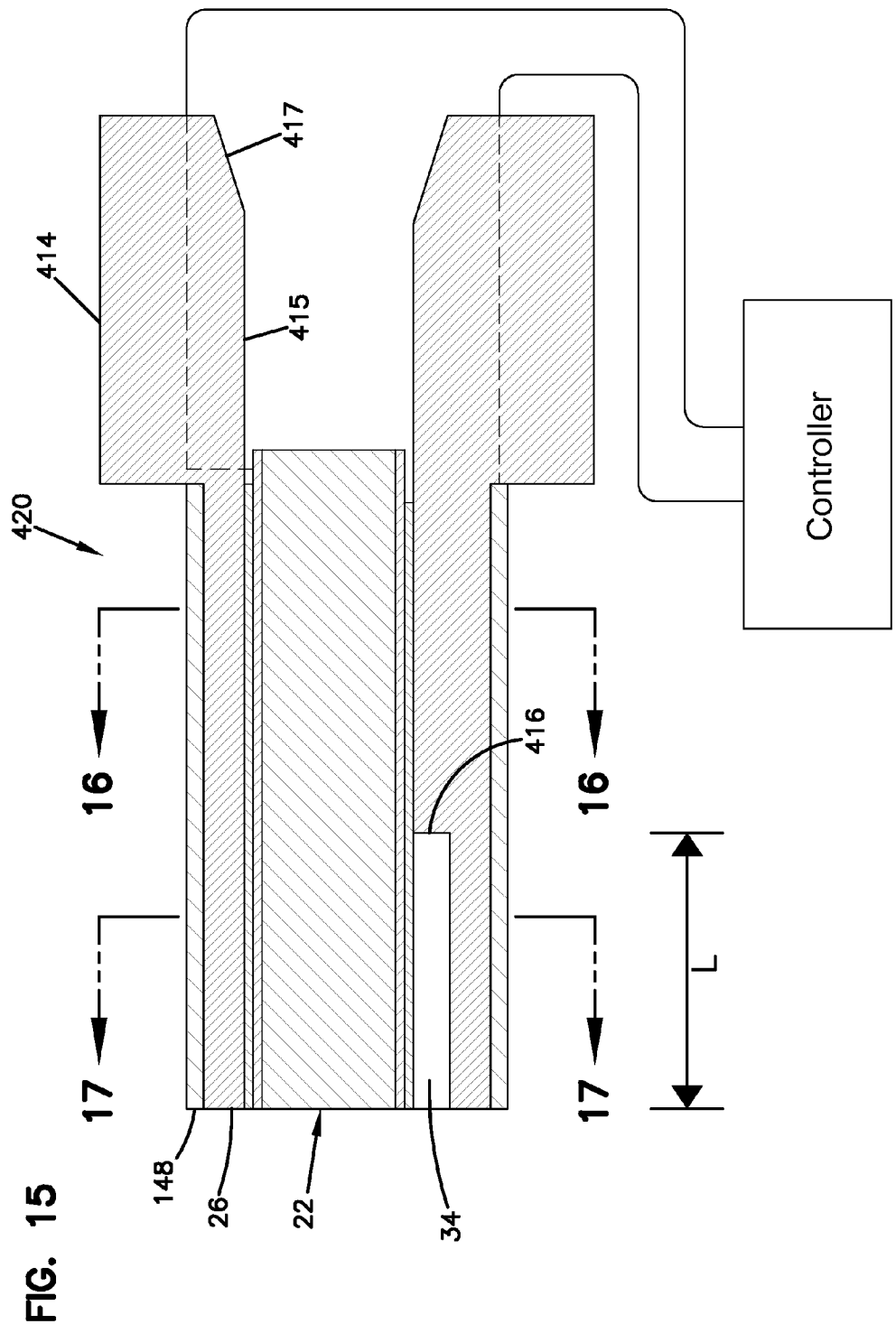
FIG. 15 shows a fifth sensor having features that are examples of inventive aspects in accordance with the principles of the present disclosure, the sensor is shown in cross-section along a section line that bisects a length of the sensor.
Figure 17:
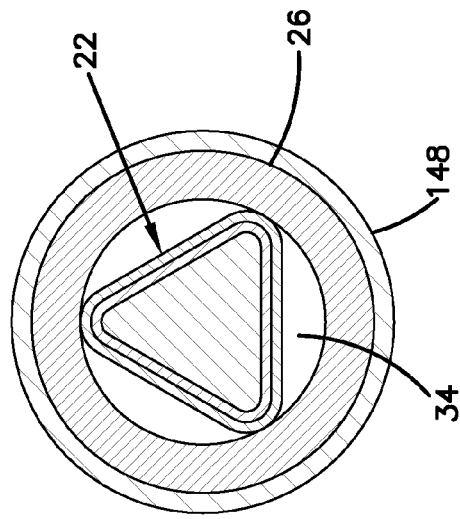
FIG. 17 is a cross-sectional view taken along section line 17-17 of FIG. 15.
Figure 16:
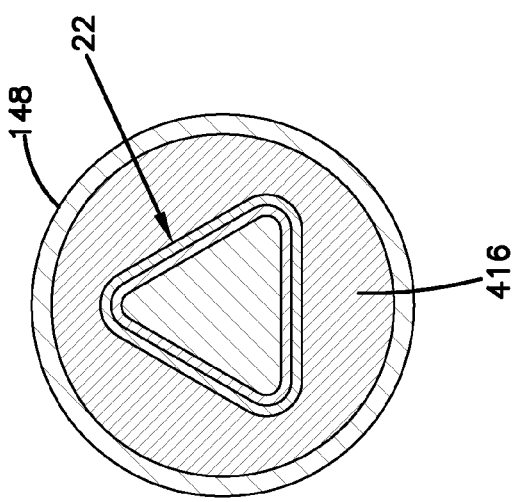
FIG. 16 is a cross-sectional view taken along section line 16-16 of FIG. 15.

FIGS. 15-17 show a fifth sensor 420 having features that are examples of inventive aspects in accordance with the principles of the present disclosure. The sensor 420 has the same general configuration as the sensor 120 of FIGS. 6 and 7, except the insulating layer 26 is integrally formed with a connector hub 414. The connector hub 414 has an opening 415 that is coaxially aligned with the inner diameter of the insulating layer 26. One end 417 of the opening 414 is tapered to facilitate inserting the elongated member 22 into the insulating layer 26. The connector hub 414 also includes integral stops 416 that fit within the channels 34 and function to prevent a sample fluid from moving within the sensor 420 a distance greater than L. As shown at FIG. 15, a controller is electrically connected to the counter and working electrodes through the connector hub 414.

Figure 18:
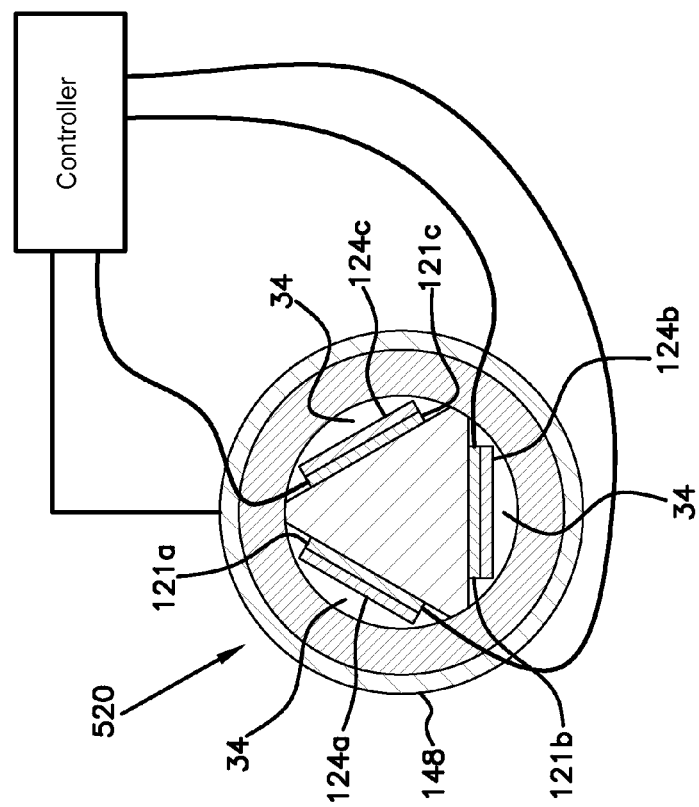
FIG. 18 shows a sixth sensor having features that are examples of inventive aspects in accordance with the principles of the present disclosure, the sensor is shown in cross-section along a section line that is transverse with respect to the length of the sensor.

FIG. 18 shows a sixth sensor 520 having features that are examples of inventive aspects in accordance with the principles of the present disclosure. The sensor 620 has the same configuration as the sensor 120 of FIGS. 6 and 7, except the working electrode has been split into three separate working electrodes 121a, 121b, 121c each corresponding to a separate channel of the sensor 520. Each of the working electrodes is provided on one side of the elongated member 22 and each working electrode is separately connected to the controller. The controller is also electrically connected to an integral counter electrode 148 provided about the insulating layer 26. The separate working electrodes can be used to detect different types of substances/materials and can be coated with the appropriate sensing layers 124a, 124b, 124c. For example, the working electrodes could be used to detect oxygen levels, lactate levels, glucose levels, catecholine levels or other material levels in a test sample and can be coated with sensing layers suitable for detecting these materials. In still other embodiments, one of the working electrodes could be used as a temperature sensor.

To manufacture sensors in accordance with the principles of the present disclosure, a conductive fiber (e.g., a Resistat® conductive fiber) is extruded or post-formed to have a desired cross sectional profile (e.g., triangular). As used herein, the term fiber includes threads, filaments, monofilaments, and other like elongated structures. The surface of the fiber is then cleaned (e.g., with an ultrasonic cleaner or degreaser), rinsed and dried. The surface can then be treated to improve its hydrophilic properties and/or can be activated with a plasma. Thereafter, the shaped fiber is passed through sequential coating stations by means of a reel to reel continuous process. At each station successive layers of sensor chemistry are applied uniformly as thin films and cured prior to entering the next station. The processed fiber is collected on storage reels for use in the succeeding step. Estimated process time is ~20 feet per minute yielding ~24,000 sub-component fibers per hour.

The cured length of fiber is collected on reels then supplied as feed stock to an assembly process where the fiber is first caused to enter a small thermoplastic molded hub (e.g., connector hub 414 of FIG. 15) having a tapered opening on one end capable of guiding the fiber preferably into an integral polyimide tube that is fixed to the opposing face of the fiber entry point and that forms the insulating layer of the sensor. The exterior of the tube 26 may be coated by various means with Ag/AgCl in order to provide an integral reference electrode 148 in concert with the working electrode of the internal fiber. In certain embodiments, the Ag/AgCl can be coated directly, or the part can be coated with Ag and then converted to an Ag/AgCl coating by oxidation of the Ag in a high Cl containing electrolyte. The connector hub can be secured to the fiber by means of sonic or induction weld to the fiber. The connector hub can include electrical connections to the working and counter electrodes and can include contact points on the connector hub that will later provide interconnection to a transmitter or output wires according to the application requirement in concert with contacts from the reference electrode. Finally, the fiber is cut to length in place within the insulator tube 26.

Suitable fixtures and "Pick and place" robotics can be used to intermittently feed the fiber into the short (e.g., 10 millimeter) hub and tube component, perform the cutting operation and place the completed sensor into carrier pallets for final assembly and packaging.

The various aspects disclosed herein provide numerous advantages. For example, the use of a chemically coated fiber covered by a separate insulator tube that is not adhered to the fiber allows for both structural enhancement and additional design flexibility. Also, the use of composite fiber as compared to pure glassy carbon fibers improves sensor durability and flexibility. Further, by using channels defined between the elongated member and the insulating layer, rapid hydration is possible thereby reducing the time required to activate the sensor. Further, the use of a fiber with an inert/dielectric core assists in blocking potential signal interference that might otherwise occur at the end of the fiber. Moreover, the cross sectional shape of the fiber/insulator interface profile is preferably not concentric but is of differing geometry, typically having multiple sides separated by angles (e.g., triangular, square, rectangular, pentagonal, hexagonal, etc). This configuration provides distinct multiple ports or channels which allow for providing different working electrodes associated with each port or channel. Using angular shaped fibers also provides limited points of contact around the insulator tube interior that both locate the fiber centrally within the tube—thus defining the port openings, as well as create minimal frictional contact between tube and fiber for ease of making a telescoping assembly of the two components. Limited point contacts also act as to prevent damage to the fragile chemistry coating from sliding surfaces between the fiber and the inner tube wall when mated in this fashion. The limited contact points also protect the sensor chemistry after assembly. For example, when the sensor is bent causing relative axial movement between the insulating layer and the conductive fiber, only the corners are subject to friction between the insulating layer and the fiber.

From the foregoing detailed description, it will be evident that modifications and variations can be made without departing from the spirit or scope of the broad inventive aspects embodied in the embodiments disclosed herein. For example, any of the embodiments disclosed herein can use separate reference and counter electrodes instead of combined counter/reference electrodes.

What is claimed is:

1. A sensor comprising:
   an elongated member including a dielectric core wherein a majority of the dielectric core is surrounded by an electrically conductive layer that forms a working electrode;
   a sensing chemistry positioned adjacent to the electrically conductive layer;
   a non-permeable insulating layer at least partially enclosing the elongated member and the sensing chemistry; and
   channels defined between the insulating layer and the sensing chemistry, the channels extending along a longitudinal axis of the elongated member.

2. The sensor of claim 1, wherein the elongated member has a diameter less than 0.02 inches.

3. The sensor of claim 1, wherein the elongated member includes a fiber.

4. The sensor of claim 3, wherein the fiber includes a composite monofilament thread material made conductive by a suffusion of the conductive layer on the dielectric core.

5. The sensor of claim 1, wherein the sensing chemistry includes a redox compound.

6. The sensor of claim 5, wherein the redox compound includes a transition metal complex with an organic ligand.

7. The sensor of claim 5, wherein the sensing chemistry includes a redox enzyme.

8. The sensor of claim 7, wherein the redox enzyme includes glucose oxidase, glucose dehydrogenase, lactate oxidase, or lactate dehydrogenase.

9. The sensor of claim 1, wherein the sensing chemistry includes a sensing layer that covers at least a portion of the conductive layer.

10. The sensor of claim 1, wherein the sensor includes a sensing tip defining an opening in the insulating layer for allowing a material to be analyzed to enter an interior of the insulating layer.

11. The sensor of claim 1, wherein the insulating layer defines an opening for allowing a material to be analyzed to reach the sensing layer.

12. The sensor of claim 1, further comprising a counter electrode carried by the insulating layer.

13. The sensor of claim 1, wherein the insulating layer has an inner cross-sectional shape that is different from an outer cross-sectional shape of the elongated member.

14. The sensor of claim 13, wherein the inner cross-sectional shape of the insulating layer is circular and the outer cross-sectional shape of the elongated member is triangular.

15. The sensor of claim 1, further comprising first and second separate working electrodes provided on the elongated member.

16. The sensor of claim 15, wherein first and second different sensing chemistries are provided on the first and second working electrodes.

17. The sensor of claim 15, wherein the elongated member includes a plurality of discrete sides, wherein the plurality of discrete sides include at least first and second sides, and wherein the first working electrode is positioned at the first side and the second working electrode is positioned at the second side.

18. The sensor of claim 1, wherein the sensor comprises at least two but no more than eight channels.

19. The sensor of claim 18, wherein the sensor comprises at least three but no more than four channels.

20. A sensor comprising:
    an elongated member including a core, the majority of the core being surrounded by a layer that is electrically conductive, the elongated member including a sensing material adapted to react with a material to be analyzed; and
    an insulating layer that surrounds the elongated member, the insulating layer defining at least one access opening for allowing the material to be analyzed to enter an interior region defined between the elongated member and the insulating layer, the insulating layer having an inner transverse cross-sectional profile that is different from an outer transverse cross-sectional profile of the elongated member, the difference in transverse cross-sectional profiles between the elongated member and the insulating layer providing channels at the interior region defined between the insulating layer and the elongated member, the channels extending generally along a length of the elongated member,
    wherein the elongated member extends along a longitudinal axis of the sensor.

21. The sensor of claim 20, further comprising a stop arrangement for limiting a distance a sample fluid can flow along lengths of the channels.

22. The sensor of claim 20, wherein the sensing material is configured to be hydrated by the material to be analyzed as the material to be analyzed moves along a length of the channels and as the analyte diffuses into the sensing layer.

23. A sensor comprising:
    an elongated member including a dielectric core surrounded at least partially by an electrically conductive layer that forms a working electrode;
    a sensing chemistry positioned adjacent to the electrically conductive layer;
    an insulating layer at least partially enclosing the elongated member and the sensing chemistry; and
    channels defined between the insulating layer and the sensing chemistry, the channels extending at least partially along a length of the elongated member,
    wherein the inner cross-sectional shape of the insulating layer is circular and the outer cross-sectional shape of the elongated member is triangular.

24. A sensor for sensing an analyte in a sample, the sensor comprising:
    a single sensing fiber defining a longitudinal axis, the single sensing fiber including an electrically conductive portion that surrounds the longitudinal axis and that extends along the longitudinal axis, the electrically conductive portion forming a working electrode, the single sensing fiber also including a sensing layer covering the electrically conductive portion, the sensing layer surrounding the longitudinal axis and having a longitudinal length that extends along the longitudinal axis; and
    a blocking layer that controls exposure of the sensing layer to the sample, the blocking layer having a side wall impermeable to the sample and configured to surround the longitudinal axis, the side wall and the sensing layer defining a longitudinal passage thereinbetween, the longitudinal passage having a passage length that extends along the longitudinal axis, the blocking layer having an open axial end for allowing the sample to enter the longitudinal passage and move longitudinally within the longitudinal passage to wet the longitudinal length of the sensing layer.

25. The sensor of claim 24, wherein the sensing fiber has a diameter less than 0.02 inches.

26. The sensor of claim 24, wherein the sensing fiber comprises a dielectric core.

\* \* \* \* \*